(12) United States Patent
Schwartz et al.

(10) Patent No.: US 7,914,540 B2
(45) Date of Patent: Mar. 29, 2011

(54) MATERIAL RETRIEVAL DEVICE AND METHOD OF USING

(75) Inventors: Bradley F. Schwartz, Springfield, IL (US); Ajay Mahajan, Murphysboro, IL (US); Jarlen Don, Carbondale, IL (US)

(73) Assignee: Board of Trustees of Southern Illinois University, Springfield, IL (US)

( * ) Notice: Subject to any disclaimer, the term of this patent is extended or adjusted under 35 U.S.C. 154(b) by 754 days.

(21) Appl. No.: 11/328,945

(22) Filed: Jan. 10, 2006

(65) Prior Publication Data

US 2006/0247662 A1 Nov. 2, 2006

Related U.S. Application Data

(60) Provisional application No. 60/675,248, filed on Apr. 27, 2005.

(51) Int. Cl.
*A61B 17/22* (2006.01)
(52) U.S. Cl. .................................................. 606/128
(58) Field of Classification Search .................. 606/200, 606/127, 114
See application file for complete search history.

(56) References Cited

U.S. PATENT DOCUMENTS

| | | | |
|---|---|---|---|
| 3,472,230 A | 10/1969 | Fogarty | |
| 4,198,960 A * | 4/1980 | Utsugi | 600/104 |
| 4,611,594 A | 9/1986 | Grayhack et al. | |
| 4,741,335 A | 5/1988 | Okada | |
| 4,790,812 A | 12/1988 | Hawkins, Jr. et al. | |
| 4,927,427 A | 5/1990 | Kriauciunas et al. | |
| 4,997,435 A * | 3/1991 | Demeter | 606/127 |
| 5,064,428 A | 11/1991 | Cope et al. | |
| 5,098,440 A | 3/1992 | Hillstead | |
| 5,190,542 A | 3/1993 | Nakao et al. | |
| 5,192,286 A | 3/1993 | Phan | |
| 5,403,324 A | 4/1995 | Ciervo et al. | |

(Continued)

FOREIGN PATENT DOCUMENTS

DE 4140007 6/1993

(Continued)

OTHER PUBLICATIONS

Office action dated Aug. 20, 2008 regarding U.S. Appl. No. 11/330,420, 23 pages.
BHA Technologies, "Consumer Fabrics," (2005) Retreived from the Internet on Nov. 16, 2005: <URL: http://www.bhatechnologies.com/consumer.htm>.
Bishoff, "The Broken Stone Basket: Configuration and Technique for Removal," J. Endourology, 15(9):911-914 (2001).
Budinski, "Engineering Materials Properties and Selection," Prentice Hall, 408-416 (1999).

(Continued)

*Primary Examiner* — Todd E Manahan
*Assistant Examiner* — Jonathan A Hollm
(74) *Attorney, Agent, or Firm* — Senniger Powers LLP (57) ABSTRACT

A medical device configured to be inserted into a patient's body to retrieve material from the patient's body includes a basket assembly. The basket assembly is configured to transition between various states including an expanded state and a collapsed state. The basket assembly may be substantially covered in a flexible sheet except for a side-facing opening when the basket assembly is in the expanded state. When the basket assembly is in the collapsed state, the side-facing opening may be substantially closed. The device may be inserted into the patient's body while the basket assembly is in the collapsed state. While in the patient's body, the basket assembly may be transitioned to the expanded state. Then, a physician may maneuver material to be removed from the patient's body into the basket assembly via the side-facing opening. Next, the basket assembly may be transitioned into the collapsed state or a partially collapsed state so that the basket assembly can be removed from the patient's body.

18 Claims, 8 Drawing Sheets

U.S. PATENT DOCUMENTS

| | | | |
|---|---|---|---|
| 5,486,183 | A | 1/1996 | Middleman |
| 5,496,330 | A | 3/1996 | Bates et al. |
| 5,499,988 | A | 3/1996 | Espiner et al. |
| 5,658,296 | A | 8/1997 | Bates et al. |
| 5,720,754 | A | 2/1998 | Middleman |
| 5,759,187 | A * | 6/1998 | Nakao et al. ............... 606/114 |
| 5,792,145 | A | 8/1998 | Bates et al. |
| 5,836,953 | A | 11/1998 | Yoon |
| 5,916,145 | A | 6/1999 | Chu et al. |
| 5,989,266 | A | 11/1999 | Foster |
| 6,004,330 | A | 12/1999 | Middleman |
| 6,096,053 | A | 8/2000 | Bates |
| 6,099,534 | A | 8/2000 | Bates |
| 6,159,220 | A | 12/2000 | Gobron |
| 6,174,318 | B1 | 1/2001 | Bates et al. |
| 6,183,482 | B1 | 2/2001 | Bates et al. |
| 6,224,612 | B1 | 5/2001 | Bates |
| 6,248,113 | B1 | 6/2001 | Fina |
| 6,264,664 | B1 | 7/2001 | Avellanet |
| 6,280,451 | B1 | 8/2001 | Bates et al. |
| 6,302,895 | B1 | 10/2001 | Gobron |
| 6,319,261 | B1 | 11/2001 | Bowers |
| 6,319,262 | B1 | 11/2001 | Bates et al. |
| 6,348,056 | B1 | 2/2002 | Bates et al. |
| 6,350,266 | B1 | 2/2002 | White et al. |
| 6,368,328 | B1 | 4/2002 | Chu |
| 6,419,679 | B1 | 7/2002 | Dhindsa |
| 6,447,523 | B1 | 9/2002 | Middleman |
| 6,520,968 | B2 | 2/2003 | Bates et al. |
| 6,527,781 | B2 | 3/2003 | Bates et al. |
| 6,551,327 | B1 * | 4/2003 | Dhindsa ..................... 606/127 |
| 6,673,080 | B2 | 1/2004 | Reynolds et al. |
| 6,695,834 | B2 | 2/2004 | Gellman et al. |
| 6,752,811 | B2 | 6/2004 | Chu |
| 6,793,666 | B2 * | 9/2004 | Hansen et al. ............... 606/200 |
| 7,018,385 | B2 | 3/2006 | Bates |
| 7,077,849 | B2 | 7/2006 | Bates |
| 7,101,379 | B2 | 9/2006 | Gregory, Jr. |
| 2002/0068943 | A1 * | 6/2002 | Chu et al. .................... 606/114 |
| 2003/0109889 | A1 * | 6/2003 | Mercereau et al. .......... 606/127 |
| 2004/0026942 | A1 | 2/2004 | Kessler et al. |
| 2004/0068271 | A1 | 4/2004 | McAlister |
| 2004/0097964 | A1 | 5/2004 | Dhindsa |
| 2005/0251151 | A1 | 11/2005 | Teague |
| 2006/0247662 | A1 | 11/2006 | Schwartz |

FOREIGN PATENT DOCUMENTS

| | | | |
|---|---|---|---|
| WO | | 0119260 A1 | 3/2001 |

OTHER PUBLICATIONS

Callister, "Materials Science and Engineering an Introduction," John Wiley and Sons, Inc., 373-393 (1997).

Dynamics Research Corporation, "Electroforming," (2005) Retreived from the Internet on Nov. 16, 2005: <URL: http://www.drc.com/metrigraphics/electroforming.htm>.

GORE Medical Products, "GORE MYCROMESH®Biomaterial" (2005) Retreived from the Internet on Nov. 16, 2005: <URL: http://www.goremedicial.com/english/products/mycromesh/Faq.htm>.

Grasso et al., "Lasers in Urology," (2005) Retreived from the Internet on Nov. 16, 2005: <URL: http://www.emedicine.com/med/topic3037.htm>.

InterNet Incorporated, "PTFE Mesh," (2000) Retreived from the Internet on Jun. 2005: URL:http://www.internetmesh.net.

Kujala, "Biocompatibility and Biomechanical Aspects of Nitinol Shape Memory Metal Implants," Dissertation, Ch. 2, (2003).

Less EMF, Inc., "EMF Shielding & Conductive Fabrics," (1996-2005) Retreived from the Internet on Nov. 16, 2005: <URL: http://www.lessemf.com/fabric.html>.

MatWeb, "Nitinol—NiTi Shape Memory Alloy; High Temperature Phase," Retreived from the Internet on Nov. 17, 2005: <URL: http://www.matweb.com/search/SpecificMaterialPrint.asp?bassnum=MTiNiO>.

Memry Corporation, "Nitinol FAQ," Retreived from the Internet on Nov. 16, 2005: <URL: http://www.memry.com/nitinolfaq/nitinolfaq.html>.

Poncet, "Nitinol Medical Device Design Considerations," MEMRY Corporation, 1-12 (2001).

Precision Eforming, "Electroformed Mesh," Retreived from the Internet on Nov. 16, 2005: <URL: http://www.precisioneforming.com/products/mesh.htm>.

Shabalovskaya, "Surface, Corrosion and Biocompatibility Aspects of Nitinol as an Implant Material," Bio-Medical Materials and Engineering, 12:69-109 (2002).

Weber, "Handbook for Laser Wavelenghts," CRC Press, 742-743 (1999).

W.L. Gore & Associates, Inc., "Instructions for Use for Gore Mycromesh®Biomaterial" (1994,1998,2004,2005) Retreived from the Internet on Nov. 16, 2005: <URL: http://www.gorematerial.com/english/products/mycromesh/Library.htm>.

Zeus, Inc., "ePTFE Tubing," (2005) Retreived from the Internet on Nov. 16, 2005: <URL:http://www.zeusinc.com/eptfe.asp>.

* cited by examiner

MATERIAL RETRIEVAL DEVICE AND METHOD OF USING

CROSS-REFERENCES TO RELATED APPLICATIONS

This application claims the benefit of U.S. Provisional Patent Application No.: 60/675,248, filed on Apr. 27, 2005, and entitled "CALCULUS ENTRAPMENT AND LITHOTRIPSY SACK," which is hereby incorporated by reference herein in its entirety for all purposes.

Additionally, this application is filed on the same day as U.S. patent application Ser. No. 11/330,420, entitled "LASER RESISTANT CALCULUS RETRIEVAL DEVICE AND METHOD OF USING," which is hereby incorporated by reference herein in its entirety for all purposes.

BACKGROUND

Urinary calculi affect roughly 1-5% of the population in the United States. Choletithiasis is found in 4-8% of people aged 40 and above. There are many devices available to entrap calculi and remove them from body cavities. Similarly there are many lithotripsy devices manufactured to fragment or fracture stones. Generally the former devices are composed of a basket or entrapment device that has three or more wires that are used to "trap" the stone. A working handle that remains extracorporeal is used to operate (mainly open and close) the wires. These devices are usually passed through an instrument, typically an endoscope, enabling the operator to directly visualize stone manipulation and/or entrapment.

It is generally recognized that urinary calculi less than or equal to 4 millimeters (mm) that make it into the ureter have an 85% chance of passing out of the urinary tract spontaneously without surgical intervention. The chance of spontaneous passage significantly diminishes as stone size increases. Stones greater than or equal to 8 mm rarely pass without interventional measures. Using only a basket or entrapment device is usually unsuccessful because the stone is too large to extract. As a result, some type of lithotripsy is typically employed.

Several prior art devices are known. For example, U.S. Pat. No. 5,064,428 to Cope et al. describes a device for retrieving calculi. The Cope et al. device includes a stone retrieval basket having three loops of nitinol wires that form a bulbous shape. The basket is connected to an inner tube having a hollow passageway. The basket and the inner tube may be inserted into a patient's body through an outer tube also having a hollow passageway. The basket may be enlarged within the body by pressing the basket against tissue. A physician then rotates and manipulates the basket to capture the calculi within the basket. Next, the inner tube is pulled outwards so that the basket collapses around the calculi and the calculi are drawn against an end of the outer tube. The physician can then insert a chemical or other well-known surgical means to dissolve, break up or crush the calculi. Fragments can be removed via the hollow passageway of the inner tube.

U.S. Pat. No. 5,403,324 to Ciervo et al. describes a device for retrieving calculi. The Ciervo et al. device includes a flexible catheter tube, and four wires pass through four hollow passageways within the catheter tube. On one end of the catheter tube, the wires exit to form a stone retrieval basket. On the other end of the catheter tube, the four wires are connected to a control mechanism that permits a physician to move the wires in and out of the catheter tube to enlarge and retract the basket. After the catheter tube is inserted in a patient's body, the physician manipulates the catheter to capture a calculus within the basket. Then, the basket is retracted to hold the calculus against the end of the catheter tube. Next, a laser or ultrasonic wire may be inserted through a fifth hollow passageway in the catheter tube to facilitate lithotripsy procedures.

U.S. Pat. No. 3,472,230 to Fogarty describes an umbrella catheter having a calculus retrieval basket comprising four spring wires that form an umbrella frame. The wires of the umbrella frame are normally bowed outwards to form a bulbous umbrella frame. The umbrella frame is partially covered on a distal end of the basket by a flexible material, such as a moldable elastomer. A control wire passes through a flexible catheter tube and is connected to a proximal end of the umbrella frame. When the control wire is pulled using a handle, the four spring wires are pulled into the catheter tube, and the umbrella is collapsed. When the control wire is pushed, the spring wires expand and the umbrella is opened. With the umbrella closed, a physician may position the umbrella beyond the location of stones or debris. Then, the physician may open the umbrella and withdraws the device a short distance to scoop up the debris. Next, the physician closes the umbrella and removes the device from the body with the stones within the umbrella.

U.S. Pat. No. 4,997,435 to Demeter describes a percutaneous catheter with an encapsulating receptacle. The Demeter device includes a first catheter with several struts connected to one end of the first catheter. The struts form a cup-shape with an opening distal from the end of the first catheter. A pocket shaped sheath is connected to the struts such that a receptacle is formed with an opening in the distal direction. A proximal portion of the sheath is connected to a second catheter passing within the first catheter. The second catheter is slidable and rotatable within the first catheter. With the struts and sheath in an untensioned condition, the opening of the receptacle is opened. But when the first catheter is rotated relative to the second catheter, the sheath twists relative to the struts causing the receptacle opening to close at the distal end. Thus, a physician can maneuver the device with the receptacle opened to capture a calculus within the receptacle. Then, the receptacle can be closed to encapsulate the calculus. The second catheter includes a lumen through which devices, such as grasping forceps, a scope, or a lithotripsy device can be inserted into the interior of the sheath.

U.S. Pat. No. 6,752,811 to Chu et al. describes several different laser-resistant medical retrieval devices. For instance, one device includes a bulbous-shaped basket formed by laser-resistant basket legs. The basket can be collapsed by retracting the basket legs within a catheter. Chu et al. explains that the basket legs can be made from or coated with laser resistant materials such as fluorocarbon plastics, ceramics, or plating of gold, silver or nickel. A laser lithotripter can be passed through the device into the basket. Chu et al. also describes a device in which the basket is partially covered on its distal end with a laser resistant fabric such as polytetrafluoroethylene (EPTFE), polytetrafluoroethylene (PTFE), tetrafluoroethylene (TFE), fluorinated ethylenepropylene (FEP), perfluoroalkoy (PFA), ethylene tetrafluoroethylene (ETFE), polyvinylidene fluoride (PVDF).

SUMMARY

A medical device configured to be inserted into a patient's body to retrieve material from the patient's body includes a basket assembly. The basket assembly is configured to transition between various states including an expanded state and a collapsed state. The basket assembly may be substantially covered in a flexible sheet except for a side-facing opening when the basket assembly is in the expanded state. When the basket assembly is in the collapsed state, the side-facing opening may be substantially closed. The device may be inserted into the patient's body while the basket assembly is in the collapsed state. While in the patient's body, the basket assembly may be transitioned to the expanded state. Then, a physician may maneuver material to be removed from the patient's body into the basket assembly via the side-facing opening. Next, the basket assembly may be transitioned into the collapsed state or a partially collapsed state so that the basket assembly can be removed from the patient's body.

In some implementations, the medical device may be configured to permit a lithotripsy device to be inserted into the basket assembly while a calculus is within the basket assembly. The flexible sheet that substantially covers the basket assembly generally helps to prevent or mitigate the migration of calculus fragments from the basket assembly during lithotripsy.

In one embodiment, a medical device may comprise a handle, and an elongated member having a proximal end and a distal end, the proximal end of the elongated member coupled to the handle. Additionally, the medical device may comprise a basket assembly coupled to the distal end of the elongated member. The basket assembly may include at least three supporting members, each supporting member having a proximal end coupled to the distal end of the elongated member and a distal end coupled to a distal end of at least one other supporting member. Each pair of adjacent supporting members may define a corresponding gap between the adjacent pair of supporting members. The basket assembly may further include a flexible sheet coupled to at least some supporting members of the at least three supporting members, the flexible sheet substantially covering all but one of the gaps, the one gap being open when the basket assembly is in an expanded state and the one gap being substantially closed when the basket assembly is in a partially collapsed state.

In another aspect, a method for treatment of material within a body includes inserting into the body a medical device. The medical device may comprise a handle, and an elongated member having a proximal end and a distal end, the proximal end of the elongated member coupled to the handle. The medical device may also comprise a basket assembly coupled to the distal end of the elongated member. The basket assembly may comprise at least three supporting members, each supporting member having a proximal end coupled to the distal end of the elongated member and a distal end coupled to a distal end of at least one other supporting member. Each pair of adjacent supporting members may define a corresponding gap between the adjacent pair of supporting members. The basket assembly may further comprise a flexible sheet coupled to at least some supporting members of the at least three supporting members, the flexible sheet substantially covering all but one of the gaps, the one gap being open when the basket assembly is in an expanded state and the one gap being substantially closed when the basket assembly is in a partially collapsed state. The method may further include maneuvering the material into the basket assembly via the one gap when the basket assembly is in the expanded state, and causing the basket assembly to transition to the partially collapsed state while the material is within the basket assembly. Additionally, the method may include causing the basket assembly to transition to a collapsed state while the material is within the basket assembly, and removing the medical device from the body.

In another embodiment, a medical device may comprise a handle, and an elongated member having a proximal end and a distal end, the proximal end of the elongated member coupled to the handle. The medical device also may comprise a basket assembly having a proximal end and a distal end, the proximal end of the basket assembly coupled to the distal end of the elongated member. The basket assembly may include at least three supporting members and a flexible sheet coupled to at least some supporting members of the at least three supporting members. The flexible sheet may substantially cover the basket assembly except for a side-facing opening when the basket assembly is in an expanded state, the side facing opening extending at least partially between the proximal end of the basket assembly and the distal end of the basket assembly in the expanded state. The side-facing opening may be substantially closed when the basket assembly is in a collapsed state.

In yet another embodiment, a method for treatment of material within a body, includes inserting into the body a medical device. The medical device may comprise a handle, and an elongated member having a proximal end and a distal end, the proximal end of the elongated member coupled to the handle. The medical device also may comprise a basket assembly having a proximal end and a distal end, the proximal end of the basket assembly coupled to the distal end of the elongated member. The basket assembly may include at least three supporting members and a flexible sheet coupled to at least some supporting members of the at least three supporting members. The flexible sheet may substantially cover the basket assembly except for a side-facing opening when the basket assembly is in an expanded state, the side facing opening extending at least partially between the proximal end of the basket assembly and the distal end of the basket assembly in the expanded state. The side-facing opening may be substantially closed when the basket assembly is in a collapsed state. The method may further comprise maneuvering the material into the basket assembly via the side facing opening when the basket assembly is in the expanded state, and causing the basket assembly to transition to the collapsed state while the material is within the basket assembly. Additionally, the method may comprise removing the medical device from the body.

DETAILED DESCRIPTION

Figure 1:
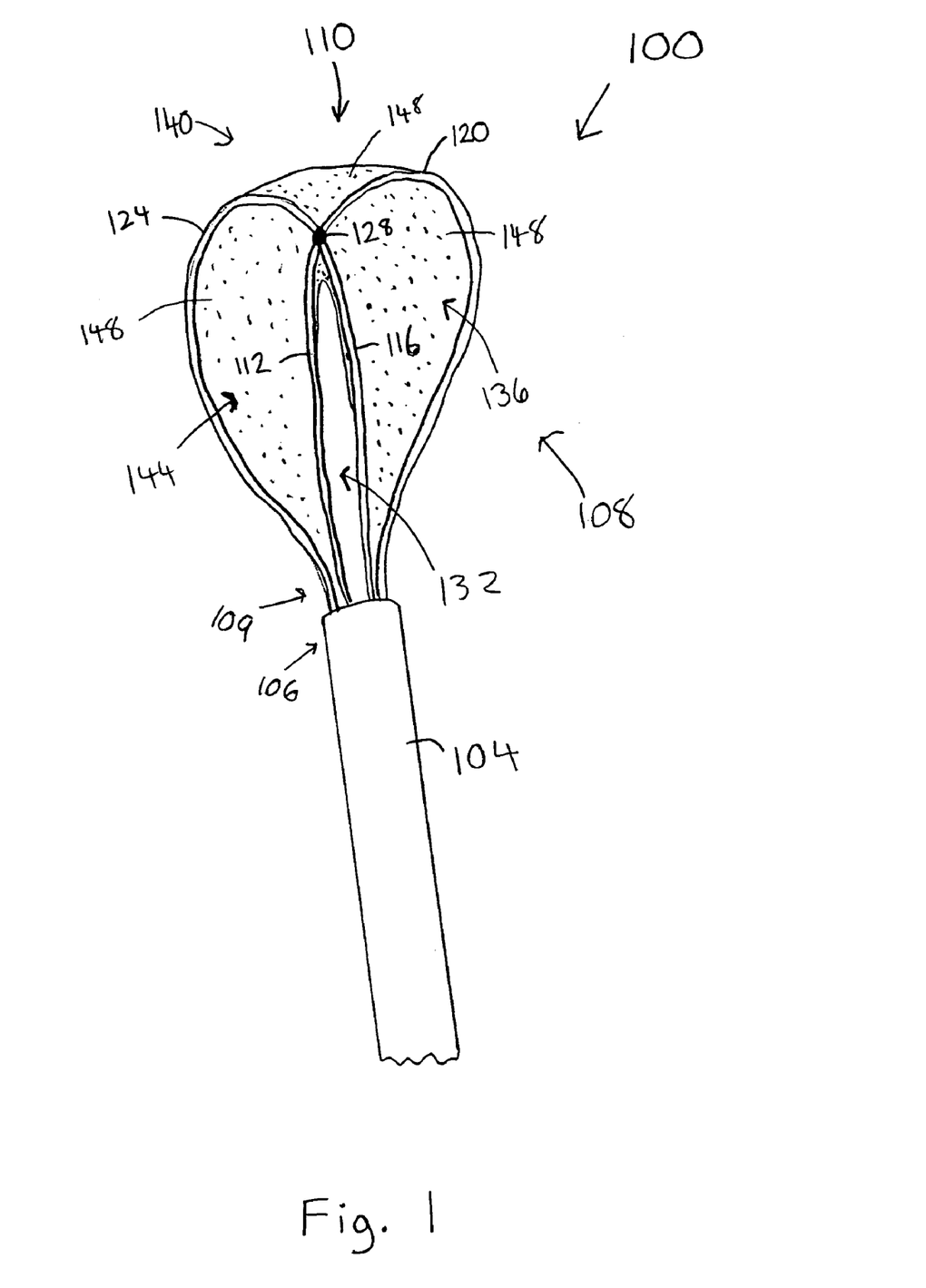
FIG. 1 is an illustration of an example of a calculus retrieval device.

FIG. 1 is an illustration of an example 100 of a calculus retrieval device. The device 100 includes a first elongated member 104 having a distal end 106 and a proximal end (not shown in FIG. 1). The device 100 also includes a basket assembly 108 having a proximal end 109 and a distal end 110. The distal end 106 of the first elongated member 104 is coupled to the proximal end 109 of the basket assembly 108. The proximal end of the first elongated member 104 may be coupled to a handle (not shown in FIG. 1) that is to remain extracorporeal. Optionally, the first elongated member 104 may include a lumen (not shown in FIG. 1) to allow another device, such as a scope, a grasping device, a lithotripsy device, etc., to be inserted into the basket assembly 108. The first elongated member 104 may have a length so that the first elongated member 104 may extend from within the patient's body to the handle. Optionally, the elongated member 104 may be much shorter. In this implementation, the elongated member 104 may be coupled to the handle by one or more other elongated members, such as a wire, a plastic member, etc., that extend to the handle.

The basket assembly 108 includes supporting members 112, 116, 120 and 124. For each supporting member, a proximal end of the supporting member is coupled to the distal end 106 of the first elongated member 104. Additionally, for each supporting member, a distal end of the supporting member is coupled to a distal end of at least one other supporting member. In the example device 100 of FIG. 1, the distal ends of the supporting members 112, 116, 120 and 124 are coupled together via a fastening mechanism 128. The fastening mechanism may comprise any of a variety of mechanisms, including known mechanisms. For example, the fastening mechanism may comprise interlocking supporting members, using a suture material, using a urethane material, using a cap, using a weld, using an adhesive, using thermal bonding, etc.

The supporting member 112 and the supporting member 120 may be integral to one another. For example, the supporting member 112 and the supporting member 120 may comprise a single looped wire. Similarly, the supporting member 116 and the supporting member 124 may be integral to one another. Thus, if the supporting member 112 and the supporting member 120 comprise a first wire and the supporting member 116 and the supporting member 124 comprise a second wire, the first wire and the second wire may be coupled together via the fastening mechanism 128. Additionally, each end of the first wire may be coupled to the distal end of the first elongated member 104, and each end of the second wire may be coupled to the distal end of the first elongated member 104. This arrangement of supporting members of a basket assembly is sometimes referred to as a tipless basket. Of course, the supporting member 112 need not be integral with the supporting member 120, and the supporting member 116 need not be integral with the supporting member 124. Such an arrangement is sometimes referred to as a tipped basket assembly. If all of the supporting members 112, 116, 120 and 124 are a single integral piece, the fastening mechanism 128 may be omitted. If the basket assembly is a tipped basket assembly, the fastening mechanism 128 may comprise a smooth covering that helps protect tissue.

Each pair of adjacent supporting members forms a corresponding gap between the adjacent supporting members. For example, the pair of supporting members 112 and 116 forms a gap 132 there between. Similarly, the pair of supporting members 116 and 120 form a gap 136 there between, and the pair of supporting members 120 and 124 form a gap 140 there between. Also, the pair of supporting members 112 and 124 forms a gap 144 there between.

A flexible sheet 148 is coupled to the basket assembly 108 such that the gaps 136, 140 and 144 are substantially covered by the flexible sheet, but the gap 132 remains substantially uncovered. Thus, the basket assembly 108 forms a substantially enclosed basket with a basket opening in the gap 132. In the example device 100 of FIG. 1, the flexible sheet 148 is coupled to an interior of the basket assembly 108. In other embodiments, the flexible sheet 148 may be coupled to an exterior of the basket assembly 108. The flexible sheet 148 may comprise a sheet permeable to liquids such as a mesh fabric, a fabric with holes cut or punched into the fabric, a sheet with holes cut or punched into the sheet etc. Also, the flexible sheet 148 may comprise a sheet impermeable to liquids, such as a non-woven material. The flexible sheet 148 may be coupled to the basket assembly 108 using a variety of techniques, including known techniques. For example, the flexible sheet 148 may be woven onto at least some of the supporting members 112, 116, 120 and 124. Also, the flexible sheet 148 may be attached to at least some of the supporting members 112, 116, 120 and 124 using fastening mechanisms such as a suture materials, urethane materials, welds, adhesives, thermal bonding, etc. Optionally, the flexible sheet 148 may be coupled to the distal end 106 of the first elongated member 104 using any of a variety of techniques, including known techniques.

Figure 2:
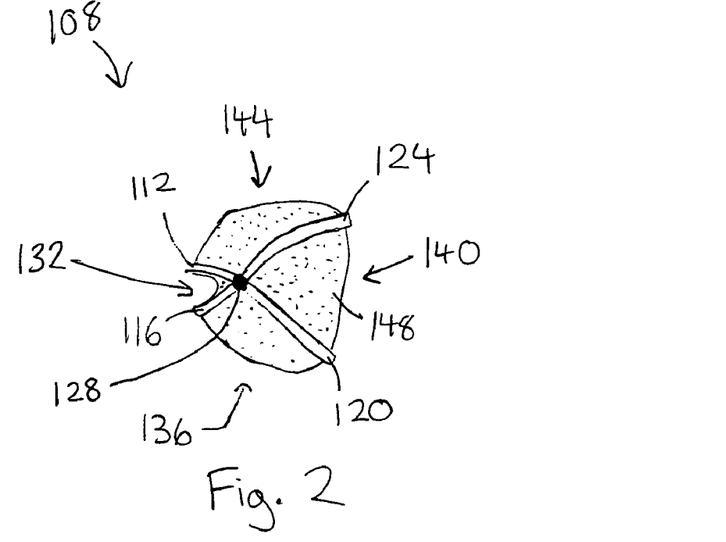
FIG. 2 is an illustration of the basket assembly of FIG. 1 viewed from its distal end.
Figure 3:
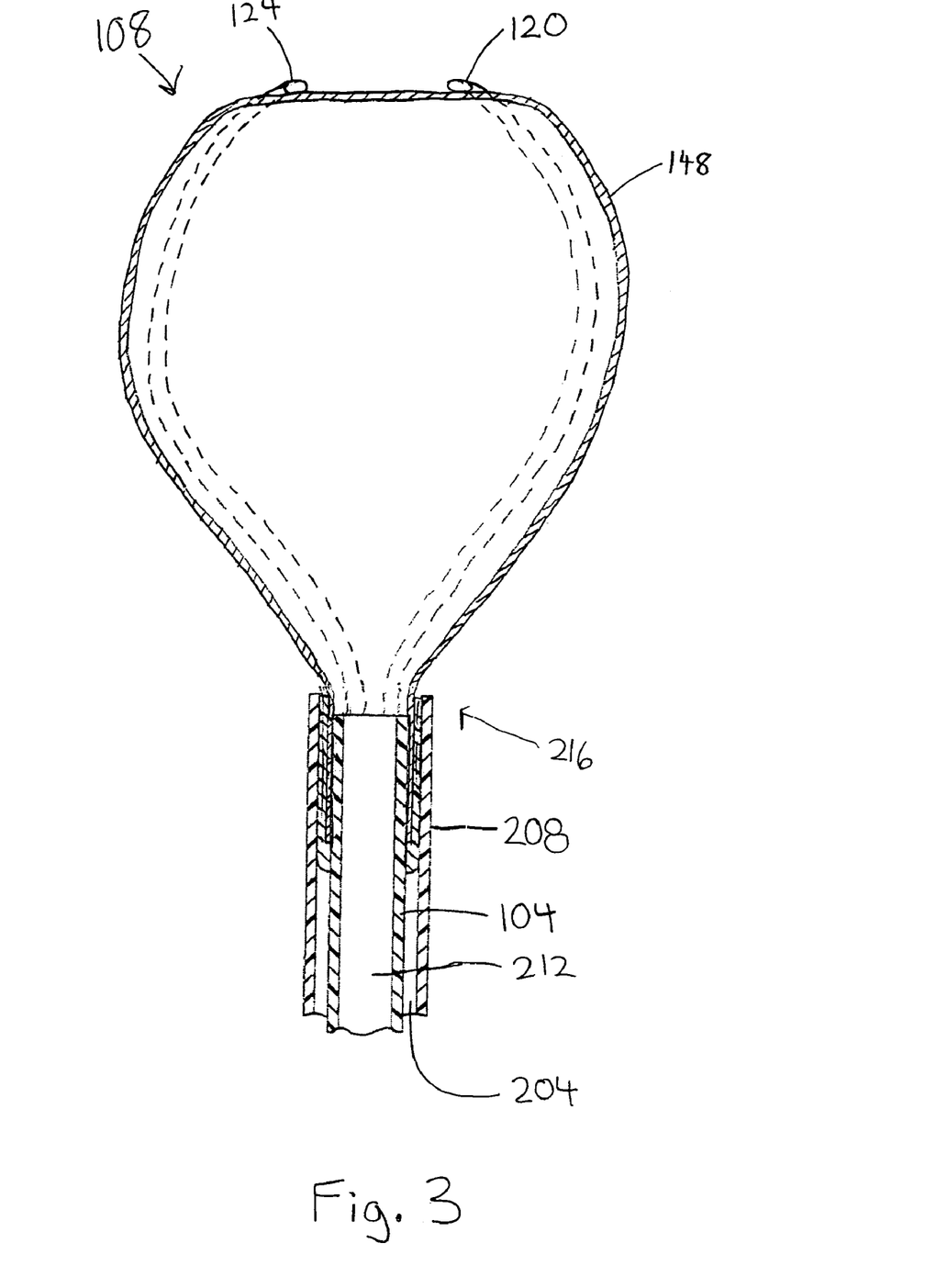
FIG. 3 is a cross-sectional view of the device of FIG. 1.

FIG. 2 is an illustration of the basket assembly 108 of FIG. 1 viewed from its distal end 110. FIG. 3 is a cross sectional view of the device 100 of FIG. 1. In FIG. 3, the first elongated member 104 is disposed within a lumen 204 of a second elongated member 208, such as a sheath, a catheter, an endoscope, etc. In the implementation shown in FIG. 3, the first elongated member 104 may include a lumen 212 through which another device, such as a scope, a grasping device, a lithotripsy device, etc., may be inserted into the interior of the basket assembly 108.

For inserting the device 100 into a patient's body, the basket assembly 108 may be positioned, in a collapsed state, within the lumen 204 of the second elongated member 208. In the collapsed state, the basket assembly 108 may be fully within the lumen 204 of the second elongated member 208. When a distal end 216 of the second elongated member 208 is positioned roughly proximate to a calculus to be removed, the basket assembly 108 may be released from the second elongated member 208 by moving the first elongated member 104 distally relative to the second elongated member 208. For example, while holding the second elongated member 208 in a substantially fixed position, the first elongated member 104 may be slid through the second elongated member 208 towards the distal end 216. As another example, the second elongated member 208 may be slid toward the proximal end of the first elongated member 104 while holding the first elongated member 104 in a substantially fixed position.

Figure 4A:
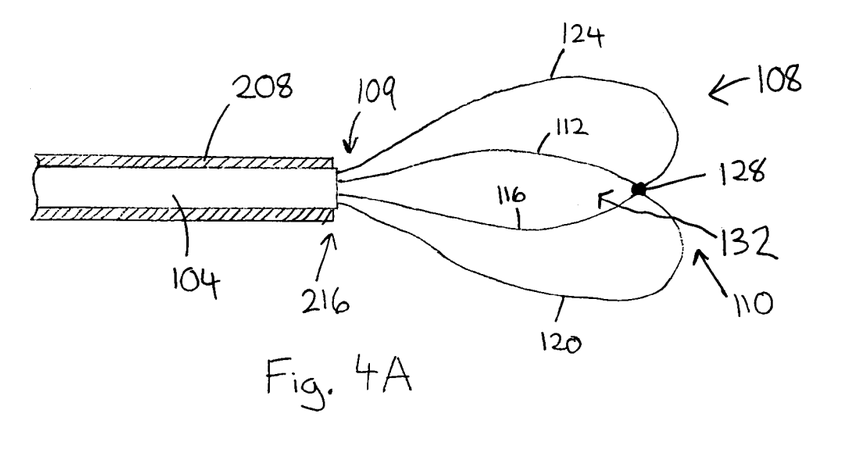
FIG. 4A is an illustration of the basket assembly of FIG. 1 in an expanded state.
Figure 4B:
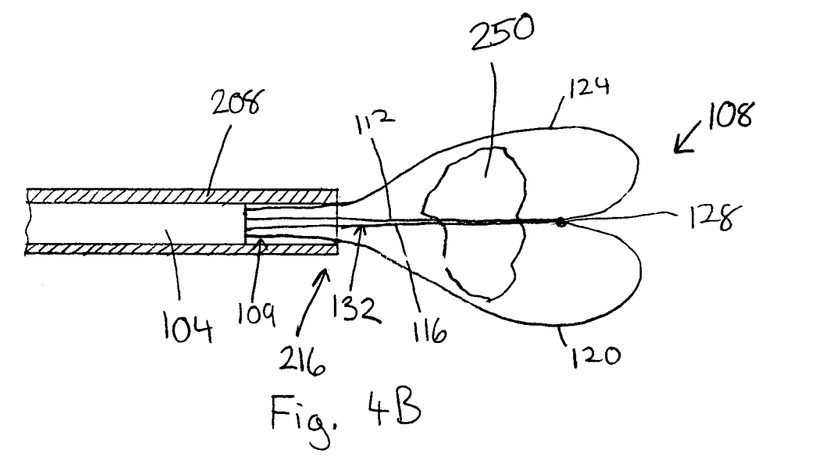
FIG. 4B is an illustration of the basket assembly of FIG. 1 in a partially collapsed state.
Figure 4C:
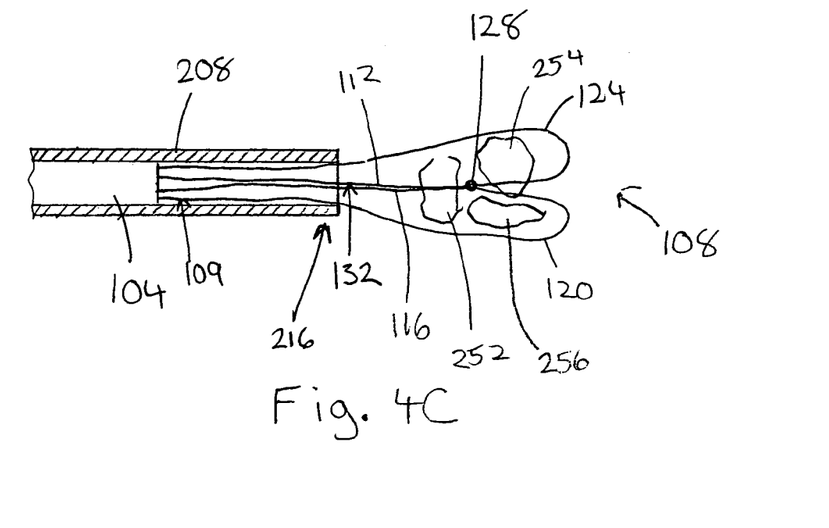
FIG. 4C is an illustration of the basket assembly of FIG. 1 in a collapsed state.

FIGS. 4A, 4B, and 4C are illustrations of the device 100 in different states. In FIGS. 4A, 4B, and 4C, the flexible sheet 148 is not shown and the second elongated member 208 is shown in cross-section for ease of explanation. Referring now to FIG. 4A, the basket assembly 108 is shown in an expanded state. In the expanded state, the gap 132 is open and the physician may thus be able to maneuver a calculus into the interior of the basket assembly 108 via the opening in the flexible sheet 148 at the gap 132. In some implementations, the physician optionally may be able to widen the gap 132 by pressing the distal end 110 of the basket assembly 108 against tissue. This may assist in maneuvering the calculus through the opening in the flexible sheet 148 at the gap 132. Also, the physician optionally may utilize additional devices such as grasping device to help maneuver the calculus through the opening in the flexible sheet 148 at the gap 132.

Referring now to FIG. 4B, the basket assembly 108 is shown in a partially collapsed state. The basket assembly 108 may be put into this state by, for example, sliding the first elongated member 104 relative to the second elongated member 208 so that the proximal end 109 of the basket assembly 108 is within the second elongated member 208. As can be seen in FIG. 4B, in the partially collapsed state, the gap 132 is substantially closed. Of course, one of ordinary skill in the art will recognize that there may be instances in which, because of the size, shape and/or position of the calculus 250, for example, the gap 132 may not be fully closed or even substantially closed in the partially collapsed state. As also can be seen in FIG. 4B, a diameter of the basket assembly 108 is substantially greater than a diameter of the second elongated member 208. The diameter of the basket assembly 108 in the partially collapsed state may be in a range of diameters of calculi that are unsafe to remove from a patient, for example.

If a calculus 250 had already been maneuvered into the interior of the basket assembly 108, the calculus 250 is substantially fully enclosed within the flexible sheet 148 of the basket assembly 108 in the partially collapsed state. Thus, for example, a calculus having a diameter too large to permit the calculus to be safely removed could be substantially fully enclosed within the flexible sheet 148 in the partially collapsed state. As will be described in more detail below, a lithotripsy device may be used to fragment such calculi. Of course, smaller calculi could also be substantially fully enclosed within the flexible sheet 148 in the partially collapsed state. Optionally, the basket assembly 108 may be transitioned back to the expanded state so that a captured calculus may be "dropped" through the gap 132 if necessary.

In some implementations, the first elongated member 104 may include a lumen through which a lithotripsy device may be inserted into the interior of the basket assembly while the basket assembly 108 is in the partially collapsed state. In these implementations, the physician may be able to break up a large calculus 250 with the lithotripsy device while the calculus 250 is fully enclosed within the flexible sheet 148. In this way, the calculus fragments may remain within the interior of the basket assembly 108.

Referring now to FIG. 4C, the basket assembly 108 is shown in a collapsed state as compared to the partially collapsed state shown in FIG. 4B. The basket assembly 108 may be put into this state by, for example, sliding the first elongated member 104 relative to the second elongated member 208 so that a substantial portion of the basket assembly 108 is within the second elongated member 208. A physician may put the basket assembly 108 into this state after breaking up the calculus 250 using a lithotripsy device, for example. FIG. 4C also illustrates that the calculus 250 has been broken into fragments 252, 254, and 256, and that these fragments remain within the interior of the basket assembly 108.

As can be seen in FIG. 4C, in the collapsed state, the gap 132 remains substantially closed. Of course, one of ordinary skill in the art will recognize that there may be instances in which, because of the size, shape, arrangement and/or positions of the calculus fragments 252, 254, and 256, for example, the gap 132 may not be fully closed or even substantially closed in the collapsed state. As also can be seen in FIG. 4C, a diameter of the basket assembly 108 is substantially smaller than the diameter in the partially collapsed state. The diameter of the basket assembly 108 in the collapsed state may permit the basket assembly 108 to be safely withdrawn from the patient's body. In some instances, a physician may be able to fully withdraw the basket assembly 108 into the second elongated member 208.

As described above with reference to FIG. 1, the proximal end of the first elongated member 104 is coupled to the handle. The handle should incorporate a device to permit a physician to cause the first elongated member 104 to be moved axially relative to the second elongated member 208 as described above with respect to FIGS. 4A, 4B, and 4C. Examples of such a device include a lever, a slide, a trigger, etc. One of ordinary skill in the art will recognize many other suitable devices. Additionally, a later-developed device may also be utilized.

The example device 100 described above generally includes a basket assembly substantially enclosed by a flexible sheet, except for a side opening. It is believed that a side opening may, at least in some circumstances, better help a physician to maneuver calculi into the basket assembly as compared to baskets having a frontal, or distal, opening. Typically, during a stone retrieval procedure, the basket is delivered via the endoscope, often making it difficult to view the distal end of a basket. Thus, a physician may, at least in some circumstances, be better able to observe calculi and the opening of the basket when the basket opening is on the side as compared to a basket having a frontal, or distal, opening.

Additionally, the basket opening of the example device 100 described above generally may be closed while the basket assembly is in a partially collapsed state. Because the basket assembly 108 of the example device 100 is substantially covered by the flexible sheet 148, and because the basket opening may be closed, a calculus can be substantially enclosed by the flexible sheet 148 when the basket assembly is in the partially collapsed state. This may help to prevent the calculus from escaping once it has been maneuvered into the basket assembly 108. If lithotripsy is to be used, substantial enclosure within the flexible sheet 148 may help prevent stone fragments from escaping the basket assembly 108 when the calculus is fragmented. This may help alleviate the need for repeated passes to remove only one or two stone fragments at a time, as is required by typical prior art devices. Additionally, this may help prevent leaving stone fragments behind. Such left behind stone fragments may cause a blockage or reformation of the stone.

If lithotripsy is to be used, the basket assembly 108 of the example device 100 generally may be further collapsed after the calculus is fragmented. In general, the basket assembly 108 elongates in the collapsed state and its diameter decreases. This permits safe removal of the device from the patient's body.

Figure 5:
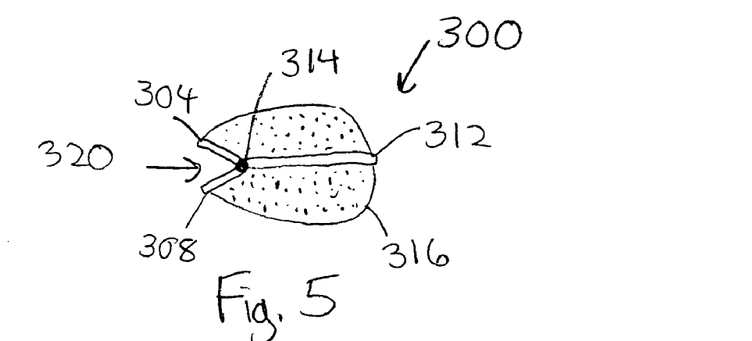
FIG. 5 is an illustration of another example of a basket assembly viewed from its distal end.

Although one example device 100 is illustrated in FIGS. 1, 2, 3, 4A, 4B and 4C, other devices having a basket assembly may be used that in which the basket assembly substantially covered in a flexible sheet, the basket assembly having a side opening that may be substantially closed in a partially collapsed state. For instance, FIG. 5 is an illustration of an example basket assembly 300 viewed from its distal end. The example basket assembly 300 includes a plurality of supporting members 304, 308 and 312. For each supporting member, a proximal end of the supporting member is coupled to a distal end of a first elongated member (not shown). Additionally, for each supporting member, a distal end of the supporting member is coupled to a distal end of at least one other supporting member. In the example basket assembly 300, the distal ends of the supporting members 304, 308 and 312 are coupled together via a fastening mechanism 314. The fastening mechanism 314 may comprise any of a variety of mechanisms, including known mechanisms. For example, the fastening mechanism may comprise a suture material, a urethane material, a cap, a weld, an adhesive, thermal bonding, etc. Two or more of the supporting members 304, 308 and 312 may be a single integral piece. If all of the supporting members 304, 308 and 312 are a single integral piece, the fastening mechanism 314 may be omitted. The basket assembly 300 may be a tipped or tipless basket.

Each pair of adjacent supporting members forms a corresponding gap between the adjacent supporting members. For example, the pair of supporting members 304 and 308 forms a gap 320 there between.

A flexible sheet 316 is coupled to the basket assembly 300 such that the gap 320 remains substantially uncovered. Thus, the basket assembly 300 forms a substantially enclosed basket with a basket opening in the gap 320. The flexible sheet 316 may be coupled to an interior or an exterior of the basket assembly 300.

Figure 6:
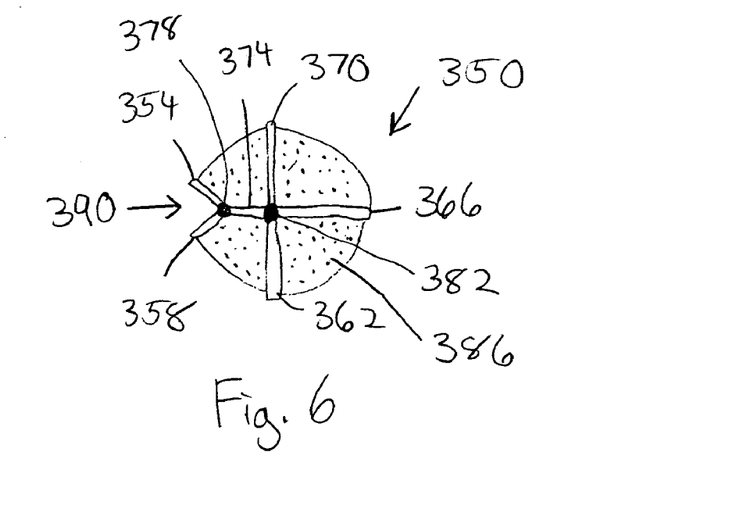
FIG. 6 is an illustration of yet another example of a basket assembly viewed from its distal end.

FIG. 6 is an illustration of an example basket assembly 350 viewed from its distal end. The example basket assembly 350 includes a plurality of supporting members 354, 358, 362, 366, 370 and 374. For each of the supporting members 354, 358, 362, 366, and 370, a proximal end of the supporting member is coupled to a distal end of a first elongated member (not shown). Additionally, for each supporting member, a distal end of the supporting member is coupled to a distal end of at least one other supporting member. In the example basket assembly 350, the distal ends of the supporting members 354 and 358 are coupled to each other as well as to a first end of the supporting 374 via a fastening mechanism 378. The distal ends of the supporting members 362, 366 and 370 are coupled to each other as well as to a second end of the supporting 374 via a fastening mechanism 382. Two or more of the supporting members 354, 358, 362, 366, 370 and 374 may be one or more single integral pieces. If all of the supporting members 354, 358, 362, 366, 370 and 374 are a single integral piece, the fastening mechanisms 378 and 382 may be omitted. The basket assembly 350 may be a tipped or tipless basket.

The pair of supporting members 354 and 358 forms a gap 390 there between. A flexible sheet 386 is coupled to the basket assembly 350 such that the gap 390 remains substantially uncovered. Thus, the basket assembly 350 forms a substantially enclosed basket with a basket opening in the gap 390. The flexible sheet 386 may be coupled to an interior or an exterior of the basket assembly 350.

In the example basket assemblies 108, 300 and 350, the supporting members between which the basket opening is located are of a shorter length than at one of the other supporting members. This is one optional aspect of a basket assembly that helps configure the basket assembly such that the basket opening will substantially close in the partially collapsed state. However, other techniques may be used to help configure a basket assembly such that the basket opening will substantially close in the partially collapsed state.

Figure 7:
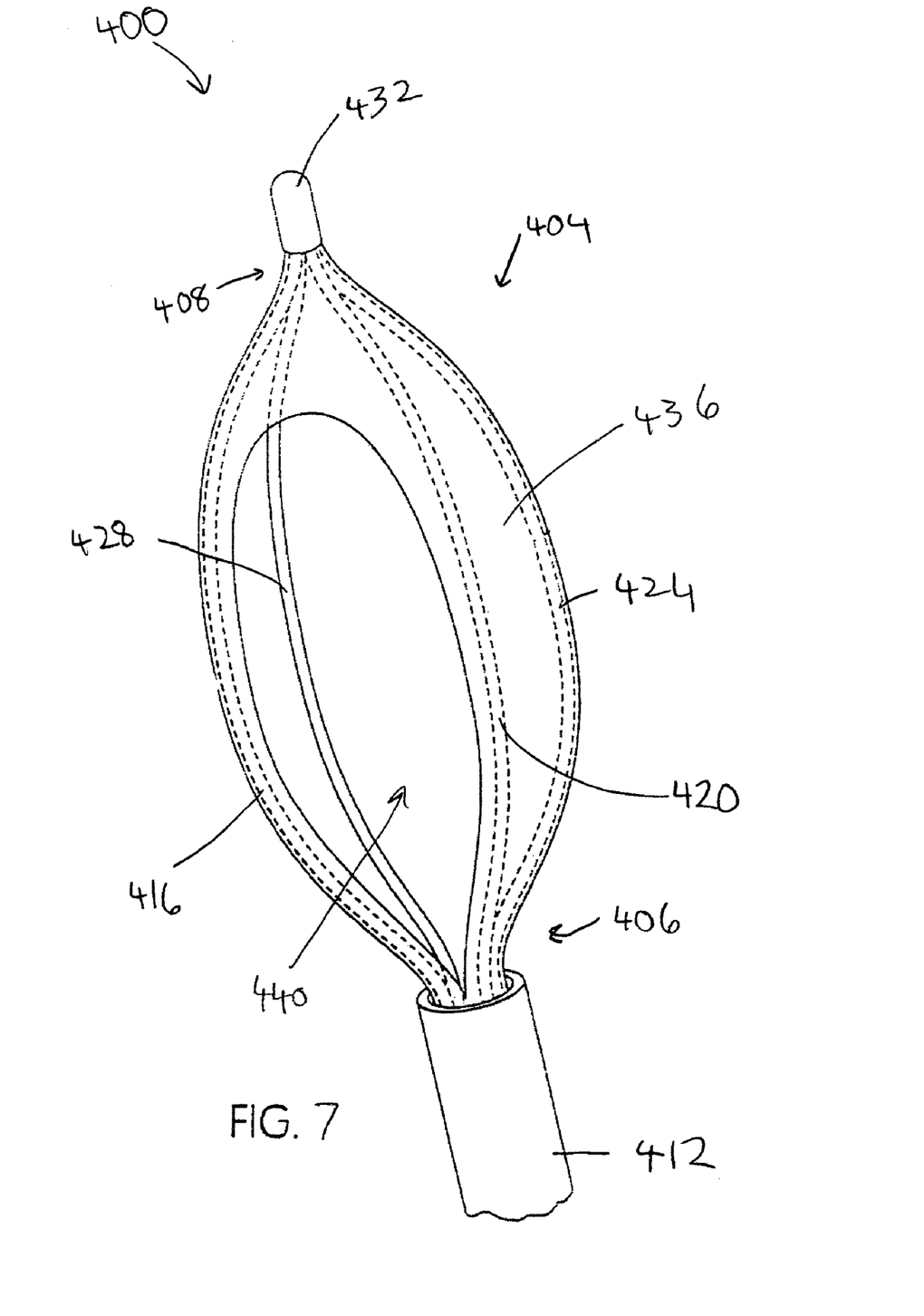
FIG. 7 is an illustration of another example of a calculus retrieval device.

FIG. 7 an illustration of an example 400 of a calculus retrieval device. The device 400 includes a basket assembly 404 having a proximal end 406 and a distal end 408. The proximal end 406 of the basket assembly 404 is coupled to a distal end of a first elongated member. In FIG. 7, the first elongated member is within a second elongated member 412.

A proximal end of the first elongated member may be coupled to a handle (not shown in FIG. 7) that is to remain extracorporeal. The first elongated member may include a lumen (not shown in FIG. 1) to allow another device, such as a scope, a grasping device, a lithotripsy device, etc., to be inserted into the basket assembly 404.

The basket assembly 404 includes supporting members 416, 420, 424 and 428. For each supporting member, a proximal end of the supporting member is coupled to the distal end of the first elongated member. Additionally, for each supporting member, a distal end of the supporting member is coupled to a distal end of at least one other supporting member. In the example device 400 of FIG. 7, the distal ends of the supporting members 416, 420, 424 and 428 are coupled together via a fastening mechanism 432. If the basket assembly 404 is a tipped basket assembly, the fastening mechanism 432 may comprise a smooth covering that helps protect tissue. The basket assembly 404 also includes a flexible sheet 436 that substantially encloses the basket assembly except for a hole 440 between the adjacent supporting members 416 and 420. The flexible sheet 436 may be coupled to an interior or an exterior of the basket assembly 404.

Figure 8A:
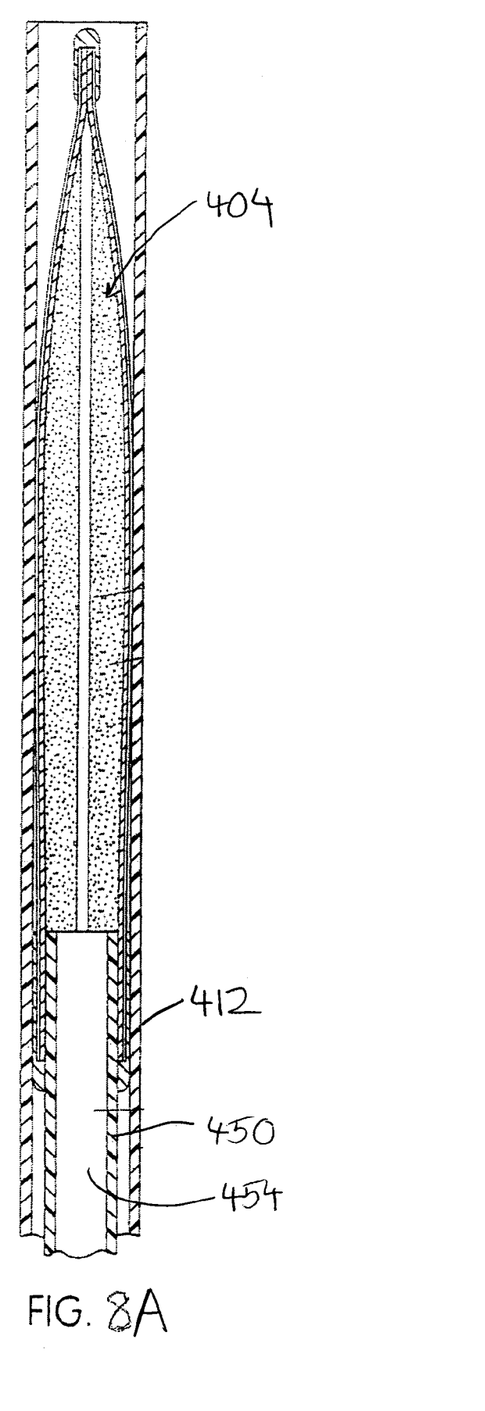
FIG. 8A is a is a cross-sectional view of a basket assembly of the device of FIG. 7 in a collapsed state and disposed within a delivery device.
Figure 8B:
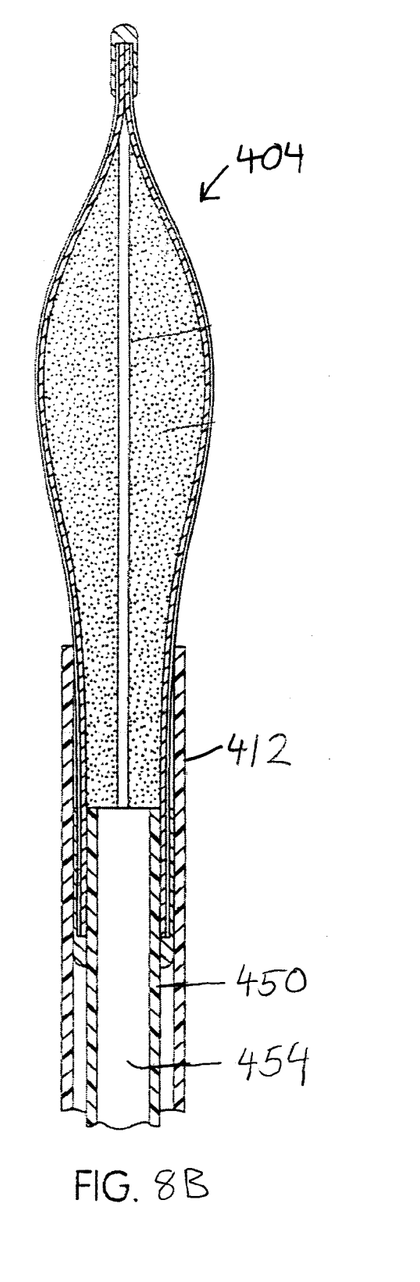
FIG. 8B is a is a cross-sectional view of the basket assembly of the device of FIG. 7 in a collapsed state and partially and deployed from the delivery device.

In FIG. 7, the basket assembly 404 is depicted in an expanded state. In FIG. 8A, a cross sectional view of the basket assembly 404 and the second elongated member 412 depicts the basket assembly 404 in a collapsed state within the second elongated member 412. Also depicted in FIG. 8A is a cross-sectional view of the first elongated member 450. The first elongated member 450 includes a lumen 454 via which to allow another device, such as a scope, a grasping device, a lithotripsy device, etc., to be inserted into the basket assembly 404. FIG. 8B depicts the basket assembly 404 in the collapsed state and partially deployed from the second elongated member 412.

Figure 9A:
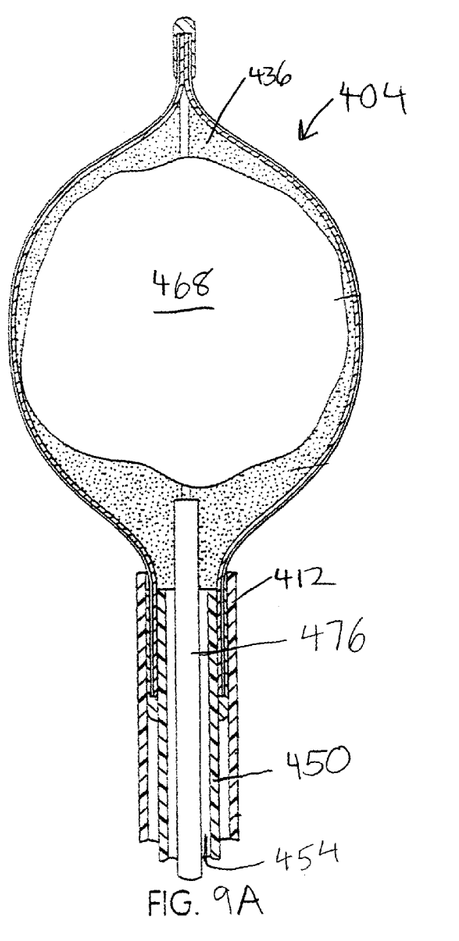
FIG. 9A is a is a cross-sectional view of the basket assembly of the device of FIG. 7 in an expanded state and with a calculus within the basket assembly.
Figure 9B:
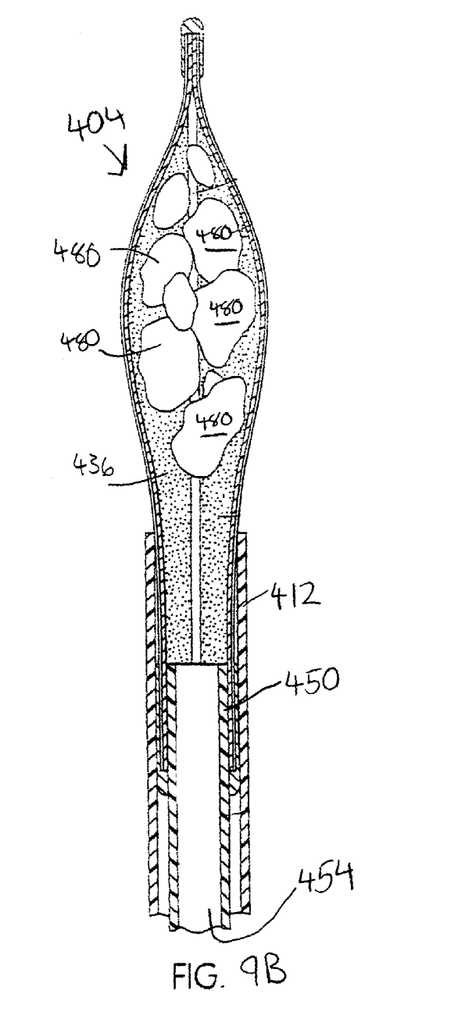
FIG. 9B is a is a cross-sectional view of the basket assembly of the device of FIG. 7 in a collapsed state and with calculus fragments within the basket assembly.

In FIG. 9A, a calculus 468 has been captured in the basket assembly 404. Additionally, a lithotripsy device 476 has been inserted into the basket assembly 404 via the lumen 454. FIG. 9B depicts the calculus 468 after it has been fragmented. The flexible sheet 436 helps to keep the fragments 480 of the calculus within the basket assembly 404. Additionally, because the calculus 468 has been fragmented, the basket assembly 404 can be transitioned to the collapsed state for removal from the patient's body.

With regard to the examples described above, in general, the supporting members of the basket assembly should comprise materials exhibiting properties that allow the basket assembly to be changed between a collapsed and an expanded state. Additionally, the materials should comprise materials that are biocompatible and, for devices that are to be used to remove kidney stones or gall stones, are compatible with urogenital fluids or bile fluids, respectively. The supporting members should be able to withstand exposure to various materials depending on the intended use of the device, such as acids, bases, salts, gases, solvents, etc., and/or various forms of energy such as mechanical energy, acoustic energy, laser energy, etc. Thus, different intended uses of the device may impose different requirements on the supporting members. Other conditions that may be taken into account in choosing a material for the supporting members include the intended service life of the device, whether it is to be used with a lithotripsy device, the type(s) of lithotripsy device with which it is intended to be used, etc. Binary nickel titanium naval ordinance laboratory (NITINOL) material is one suitable material. One of ordinary skill in the art will recognize other suitable materials as well, such as metals, steel, etc. Further, new suitable materials may be developed in the future.

With regard to the flexible sheet, it should comprise materials exhibiting properties that allow the basket assembly to be changed between a collapsed and an expanded state. Additionally, the materials should comprise materials that are biocompatible and, for devices that are to be used to remove kidney stones or gall stones, are compatible with urogenital fluids or bile fluids, respectively. In general, the flexible sheet should be able to withstand exposure to various materials depending on the intended use of the device. For example, depending on the intended use, the flexible sheet may be exposed to materials such as acids, bases, salts, gases, solvents, etc., and/or various forms of energy such as mechanical energy, acoustic energy, laser energy, etc. Thus, different intended uses of the device may impose different requirements on the flexible sheet. Other conditions that may be taken into account in choosing a material for the flexible sheet include the intended service life of the device, whether it is to be used with a lithotripsy device, the type(s) of lithotripsy device with which it is intended to be used, etc. In general, a variety of material could be used including ceramics, polymers, metals carbon fibers/composites, etc.

Figure 10:
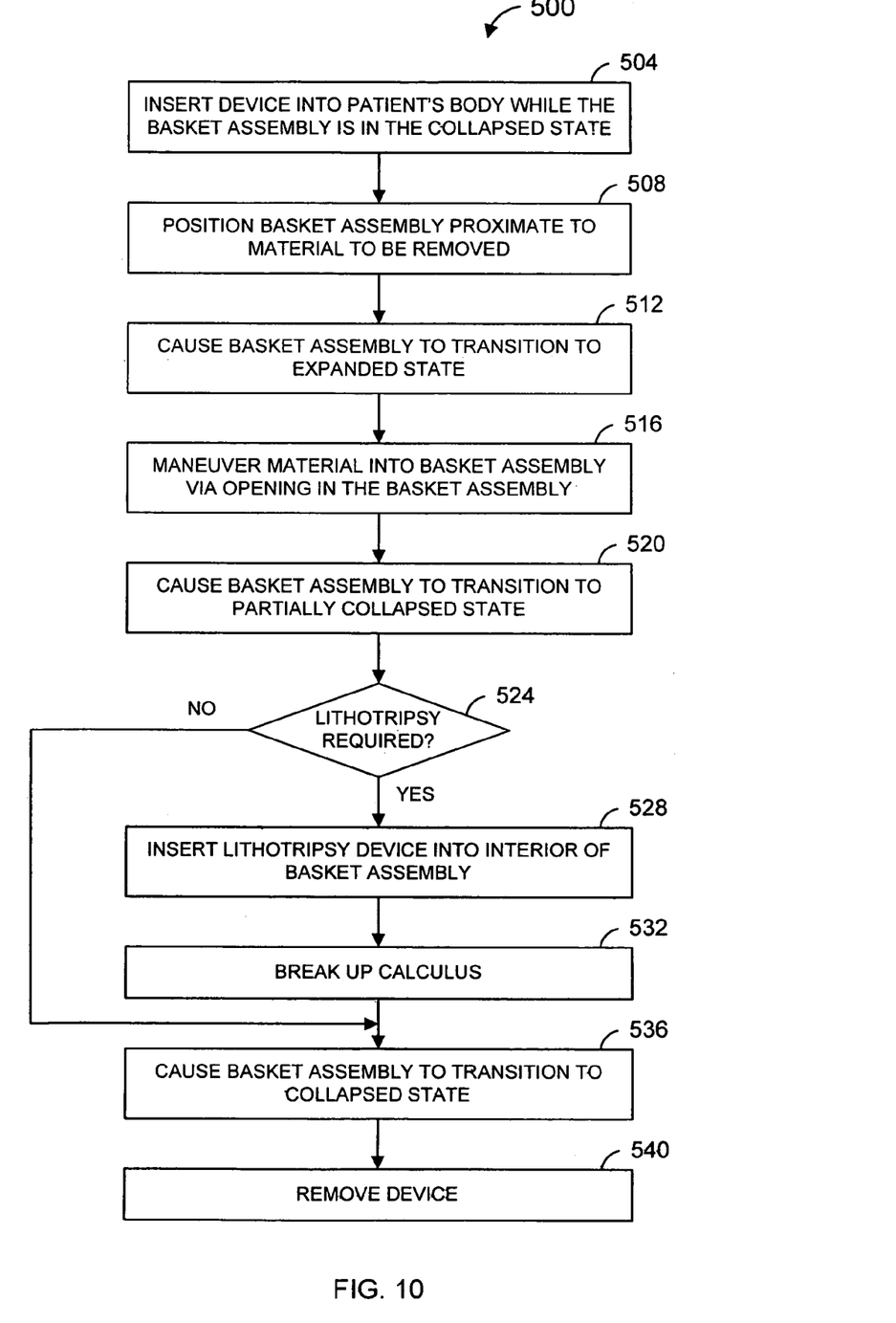
FIG. 10 is a flow diagram of an example method for using a device to remove material from a body.

FIG. 10 is a flow diagram of an example method 500 for retrieving material from a patient's body using a device such as the example devices described above. For ease of explanation, the method 500 will be described with reference to the example device 100. However, it will be understood by those of ordinary skill in the art that the method may be performed using other devices, such as the other devices described above, as well. At a block 404, the device 100 may be inserted into the patient's body while the basket assembly 108 is in the collapsed state. For example, the basket assembly may be enclosed within a casing, sheath, catheter, endoscope, ureterscope, etc. (hereinafter "delivery device"), and in the collapsed state, and the delivery device may be inserted into the patient's body. The device 100 may be inserted into the delivery device prior to or after the delivery device is inserted into the body.

At a block 508, the basket assembly 108 is positioned proximate to the material to be removed. This may comprise, for example, positioning an end of the delivery device proximate to the material while the basket assembly 108 is proximate to the end of the delivery device. As another example, the end of the delivery device may first be positioned proximate to the material, and then the basket assembly 108 may be moved proximate to the end of the delivery device.

At a block 512, the physician may cause the basket assembly 108 to transition to the expanded state. For example, the physician may cause the basket assembly 108 to exit from the end of the delivery device. This may comprise, for example, causing the first elongated member 104 to slide relative to the second elongated member 208 and within the lumen 204 of the second elongated member 208 in a direction toward the distal end 216 of the second elongated member 208. The physician may use a handle, a lever, a slide, a trigger, etc., to cause the cause the basket assembly 108 to exit from the end of the delivery device. As described above, the side opening of the basket assembly 108 may help in maneuvering the material into the basket assembly 108 as compared to a front or distal opening basket.

At a block 516, the physician may maneuver the material into the basket assembly 108 via the side opening in the gap 132. For example, the physician may maneuver the basket assembly 108 within the patient using a handle of the device 100. Optionally, the physician may utilize a separate device, such as a grasping device, to maneuver the material into the basket assembly 108. Maneuvering the material into the basket assembly 108 may optionally comprise pressing the distal end 110 of the basket assembly 108 against tissue to cause the gap 132 to widen.

After the material is within the basket assembly, the physician may cause the basket assembly 108 to transition to the partially collapsed state. This may comprise, for example, retracting the basket assembly 108 partially within the delivery device. Such a retraction may comprise, for example, causing the first elongated member 104 to slide relative to the second elongated member 208 and within the lumen 204 of the second elongated member 208 in a direction away from the distal end 216 of the second elongated member 208. The physician may use a handle, a lever, a slide, a trigger, etc., to cause the cause the basket assembly 108 to retract partially within the delivery device. As described above, in the partially collapsed state, the gap 132 in the basket assembly 108 is substantially closed.

Blocks 524, 528 and 532 may be performed if the device 100 includes the lumen 212 in the first elongated member 104. If the device 100 does not include the lumen, blocks 524, 528 and 532 optionally may be omitted. At the block 524, it may be determined if lithotripsy is required. For example, it may be determined if a calculus has a diameter that is too big to allow it to be safely removed from the patient's body using the device 100. If it is determined that lithotripsy is required, the flow may proceed to the block 528.

At the block 528, a lithotripsy device may be inserted into the interior of the basket assembly 108 via the lumen 212. The lithotripsy device used may be any of a variety of lithotripsy devices such as a mechanical device, a device to deliver a chemical to the calculus, an acoustic device, a laser device, an electrohydraulic lithotripsy device, etc. Then, at the block 532, the calculus may be broken up using the lithotripsy device. Because the basket assembly 108 is substantially enclosed by the flexible sheet 148, fragments of the calculus should generally remain within the basket assembly 108.

If lithotripsy was not required or if the calculus was broken up, the physician, at the block 536, may cause the basket assembly 108 to transition to the collapsed state. This may comprise, for example, retracting the basket assembly 108 more fully within the delivery device. Such a retraction may comprise, for example, causing the first elongated member 104 to slide relative to the second elongated member 208 and within the lumen 204 of the second elongated member 208 in a direction away from the distal end 216 of the second elongated member 208. The physician may use a handle, a lever, a slide, a trigger, etc., to cause the cause the basket assembly 108 to retract more fully within the delivery device.

Then, at the block 540, the physician may remove the device. This may comprise, sliding the device 100 through and out of the delivery device while the delivery device remains in the patient's body. This may also comprise removing the delivery device from the patient's body while the device 100 is disposed within the delivery device.

Referring again to FIG. 1, in implementations in which a laser lithotripsy device is to be used with the device 100, the flexible sheet 148 and/or the supporting members 112, 116, 120 and 124 may comprise materials resistant to damage by a laser. Additionally, the flexible sheet 148 and/or the supporting members 112, 116, 120 and 124 may be configured to increase resistance to damage by a laser. A direct hit by a lithotripsy laser could cause a wire of a typical calculus retrieval basket to break or fragment. As is well known to those of ordinary skill in the art, fragmentation or breakage of a calculus retrieval basket while in the patient's body is an extremely adverse event.

The cross-sectional shape of the supporting members may affect their resistance to damage by a laser. Bishoff, "The Broken Stone Basket: Configuration and Technique for Removal," J. Endourology, 15(9), pp. 911-13 (2001) (hereinafter "Bishoff") states that baskets with "round wires and smaller diameters tend to require less energy for breakage than the flat wire baskets." Thus, wires that are flat may tend to be more laser resistant than wires that are round. Also, increasing the cross-sectional area of a wire may tend to increase its laser resistance.

Table 1 lists energy levels, provided by Bishoff, required to break wires in various commercially available stone retrieval baskets. Each of the baskets listed in Table 1 is formed from wires made of NITINOL material.

TABLE 1

| Basket | Laser Energy Level Required to Fragment Basket Wire |
| --- | --- |
| 3.0F N-Circle | 0.02 kJ |
| 2.4F Zero Tip | 0.03 kJ |
| 3.0F Segura | 0.06 kJ |
| Platinum Class 3.0F Helical Wire | 0.07 kJ |
| Platinum Class 2.4F Flat Wire | 0.10 kJ |
| 3.0F Gemini | 0.15 kJ |
| 3.2F Captura | 0.63 kJ |
| 4.5F N-Force | 0.67 kJ |
| 3.2F Atlas | 0.78 kJ |

Two types of lasers are typically used in urological applications: the Holmium: yttrium-aluminum-garnett (Ho:YAG) laser and the Neodymium: yttrium-aluminum-garnett (Nd:YAG) laser. The Ho:YAG laser emits energy in a pulsating manner and the absorption depth of tissue is typically 1-2 millimeters (mm) when it is employed in a $H_2O$ based medium. The light energy of the Ho:YAG laser provides good hemostasis when used in a pulsating mode of 250 milliseconds (ms) duration at 10 Hz and 1.6 Joules/pulse. The Ho:YAG laser superheats $H_2O$ which absorbs the light energy. Ho:YAG laser is mid-infrared which absorbs well with $H_2O$. On the other hand, the Nd:YAG laser is near infrared and is delivered in a continuous pulsating manner. The wavelength ($\lambda$) for Ho:YAG laser is 2.1 micrometers ($\mu$m) and has a typical energy output of 1-5 Joules. The wavelength for Nd:YAG laser is 1.064 $\mu$m.

Since the 1980's, NITINOL materials have been increasingly used for a variety of medical devices. A direct firing of a Ho:YAG laser on a NITINOL wire may cause the wire to fragment. Binary NITINOL is primarily used for medical devices. Binary NITINOL has an optimum superelastic behavior at body temperature which is approximately 38° C.

One technique for improving the laser resistance of a wire such as a NITINOL wire is to coat it, at least partially, with a laser resistant coating. Such a coating may comprise one or more of a ceramic material, a fluorocarbon plastic, platings of gold, silver, nickel, etc., polished to a reflective surface, etc. With respect to cost, a ceramic or polymer type composite could possibly be more cost effective than other coatings if the calculus retrieval device is to be discarded after one procedure. But a coating technique may have drawbacks. For instance, it may be difficult to get the coating to adequately adhere to the wire. Also, the deformation of the basket during use may cause cracking of coatings. Further, a coating of a material may cause cracking or change the flexibility of the wires. Moreover, coatings that require heat greater than 300° C. may be unusable with a NITINOL wire because the heating may change the flexibility and properties of the wire.

Referring again to FIG. 1, if the flexible sheet 148 is laser resistant, if the flexible sheet 148 is coupled to an interior of the basket assembly 108, and if a laser lithotripsy device is to be used within the interior of the basket assembly 108, then the flexible sheet 148 may help protect the support members 112, 116, 120 and 124 from damage from a laser. (Of course, in other implementations, the flexible sheet 148 may be coupled to an exterior of the basket assembly 108 even if a laser lithotripsy device is to be used within the interior of the basket assembly 108.) A laser resistant flexible sheet 148 may be comprised of a variety of materials such as polymers, carbon fibers, ceramics, gold, silver, polished nickel, copper, carbon fibers/composites, etc.

Fluorocarbon polymers, such as expanded polytetrafluoroethylene (ePTFE), are resistant to the Ho:YAG laser. Medical grade expanded ePTFE is microporous, and therefore, have minimal environmental moisture absorption. Also, ePTFE is biocompatible, soft, and flexible, has increased linear strength, and has a low dielectric constant. One example of an ePTFE fabric is MYCROMESH® mesh material made by W. L. Gore & Associates. This mesh material is made of ePTFE and has a microporous structure. The MYCROMESH® material is used for hernia repair and it is believed that it is not generally laser resistant. InterNet, Inc. has developed a polytetrafluoroethylene (PTFE) mesh, which InterNet, Inc. believes it is neither microporous nor laser resistant. InterNet also asserts that it is suitable for high temperature applications and it is generally chemically resistant. In general, ePTFE and/or PTFE meshes may be microporous or non-microporous depending on the intended application. Similarly, ePTFE and/or PTFE meshes may be laser resistant or not laser resistant depending on the intended application.

There are currently available silver-coated polymer (nylon) mesh fabrics. Two examples of these fabrics a high performance silver mesh fabric and a see-thru conductive fabric are described at http://www.lessemf.com/fabric.html. The high performance silver mesh fabric comprises a stretchy silver-coated nylon weave. This particular mesh material will shield low intensity radiofrequency and microwaves, and may be an excellent electric field shield when grounded. This silver mesh fabric material weighs 40 g/m$^2$, has a temperature range of $-30°$ C. to 90° C., and has an electrical resistivity of less than 0.5 $\Omega$/m. The see-thru conductive fabric is a stretchy sheer nylon weave. This particular material will shield a low intensity radiofrequency and microwaves. It is an excellent electric shield when grounded. The fabric is a diamond shaped knit pattern and weighs 0.3 oz/yd$^2$.

A company called Precision Eforming developed a variety of lightweight flexible materials by electroforming mesh fabrics. Electroforming involves using an electrolytic bath to deposit an electroplatable metal onto a conductive patterned surface. Precision Eforming produces a range of mesh electroformed material from copper, gold, and nickel.

In general, if the flexible sheet 148 that is to be laser resistant, it may comprise a material such as ePTFE, PTFE, tetrafluoroethylene (TFE), fluorinated ethylenepropylene (FEP), perfluoroalkoy (PFA), ethylene tetrafluoroethylene (ETFE), polyvinylidene fluoride (PVDF), etc. Also, the flexible sheet 148 may comprise a ceramic material, a plating of gold, silver, nickel, etc., polished to a reflective surface, etc.

With regard to the structure of the basket assembly 108, Bishoff has found that basket assemblies with a tip tend to be less prone to breaking from a laser as compared to basket assemblies without a tip. It is believed that tipped baskets, when broken, tend to have broken segments that outwardly protrude. With tipless baskets, broken segments tend to have less change in their shape as compared with broken tipped baskets.

In one particular implementation in which the device 100 is to be used with a laser lithotripsy device, the supporting members 112 and 120 comprise a first NITINOL wire and the supporting members 116 and 124 comprise second NITINOL wire. In this particular implementation, the flexible sheet 148 comprises an ePTFE fabric. One of ordinary skill in the art will recognize that, in other implementations, other materials may be used. Additionally, instead of the supporting members 112, 116, 120 and 124 comprising two separate wires, the supporting members 112, 116, 120 and 124 could comprise four separate wires, for example.

Table 2 lists results of an experiment in which a PTFE mesh was coupled to the inside of a tipless NITINOL wire basket, and a PTFE mesh was coupled to the outside of a tipless NITINOL wire basket. Each of these baskets was then shot within by a Ho: YAG laser. As can be seen in Table 2, placing the PTFE mesh within the basket appeared to help protect the NITINOL wires from damage.

TABLE 2

| Position of PTFE Mesh | Degree of Damage From Ho: YAG laser |
| --- | --- |
| Mesh Inside Basket | Little Damage to NITINOL Basket Wires; no damage to PTFE mesh |
| Mesh Outside Basket | Damage to NITINOL Basket Wires; no damage to PTFE mesh |

Table 3 lists results of an experiment in which a PTFE mesh was placed over a thin NITINOL wire, and placed over a thick NITINOL wire basket.

TABLE 3

| Size of NITINOL Wire | Degree of Damage From Ho: YAG laser |
| --- | --- |
| Thin | NITINOL wire damaged; no damage to PTFE mesh |
| Thick | NITINOL wire broke for one testing; no damage to PTFE mesh |

Table 4 lists results of an experiment in which mesh materials were shot by a Ho: YAG laser while the mesh materials were in various environments.

TABLE 4

| Material | Material in Air | Material in Bowl of Water | Material in Cup of Alkaline Fluid (8.4% sodium bicarbonate solution; pH of about 8.3) | Material in Cup of Acidic Fluid (0.25% acetic acid solution; pH of about 3.1) |
| --- | --- | --- | --- | --- |
| PTFE | No Damage | No Damage | No Damage | No Damage |
| ePTFE | No Damage | No Damage | No Damage | No Damage |
| High Performance (HP) Ag Nylon | Mesh damaged, hole burned through sample | Mesh damaged, hole burned through sample | n/a | n/a |
| High Performance (HP) Ag Nylon | n/a | Mesh damaged, hole burned through sample | n/a | n/a |
| See-Thru (ST) Ag Nylon | n/a | Mesh damaged, hole burned through sample | n/a | n/a |
| Gold | n/a | Mesh damaged, hole burned through sample | n/a | n/a |
| Nickel | n/a | Mesh damaged, hole burned through sample | n/a | n/a |

Of the samples tested, it appeared that PTFE mesh and a 240-480 micron ePTFE sheet withstood the Ho: YAG laser better than the other materials under the various conditions. In general, a thinner mesh is more flexible but may have less strength. It is currently believed by the inventors that a PTFE mesh or an ePTFE mesh with a thickness generally in the range of approximately 100-300 microns would provide appropriate laser resistance, strength, and flexibility. However, other thicknesses may also be adequate, such as a thickness less than 100 microns or greater than 300 microns. Additionally, an appropriate thickness may vary depending upon the material to be used. Further, it is to be understood the fabric need not comprise PTFE or ePTFE.

While the invention is susceptible to various modifications and alternative constructions, certain illustrative embodiments thereof have been shown in the drawings and are described in detail herein. It should be understood, however, that there is no intention to limit the disclosure to the specific forms disclosed, but on the contrary, the intention is to cover all modifications, alternative constructions and equivalents falling within the spirit and scope of the disclosure as defined by the appended claims.

What is claimed is:

1. A medical device, comprising:
   a handle;
   an elongated member having a proximal end and a distal end, the proximal end of the elongated member being coupled to the handle; and
   a basket assembly attached to the distal end of the elongated member, the basket assembly comprising a group of at least three supporting members, each supporting member having a proximal end coupled to the distal end of the elongated member and a distal end coupled to a distal end of at least one other supporting member, each pair of adjacent supporting members in the group defining a corresponding gap between the pair, the basket assembly further comprising a flexible sheet attached to at least some of the supporting members in the group, the flexible sheet substantially covering all but one of the gaps, the one gap being open when the basket assembly is in an expanded state and the one gap being substantially closed when the basket assembly is in a partially collapsed state, wherein said basket assembly is substantially free of elongated support members extending laterally across the gaps wherein the pair of supporting members defining the one gap have lengths shorter than at least one other supporting member in the group and wherein the distal ends of the pair of supporting members defining the one gap are directly attached to one another at a point offset from an axis extending distally from the distal end of the elongated member.

2. A medical device according to claim 1 wherein said elongated member is a first elongated member and said medical device further comprises a second elongated member having a lumen, wherein the first elongated member is disposed at least partially within the lumen, the first elongated member capable of moving axially within the lumen relative to the second elongated member.

3. A medical device according to claim 1, wherein the elongated member includes a lumen to permit insertion of a device into the basket assembly via the distal end of the first elongated member.

4. A medical device according to claim 3, wherein the device is a laser lithotripsy device.

5. A medical device according to claim 1, wherein the group of supporting members comprises four supporting members.

6. A medical device according to claim 5, wherein the group of four supporting members comprises four separate supporting members coupled together by a fastening mechanism.

7. A medical device according to claim 5, wherein a first pair of the group of four supporting members forms a first integral member and a second pair of the group of four supporting members forms a second integral member, wherein the first integral member is coupled to the second integral member with a fastening mechanism.

8. A medical device according to claim 5, wherein the group of four supporting members comprises a single integral member.

9. A medical device according to claim 1, wherein the flexible sheet comprises an unwoven material.

10. A medical device according to claim 1, wherein the flexible sheet comprises a mesh fabric.

11. A medical device according to claim 1, wherein the flexible sheet is on an interior of the basket assembly.

12. A medical device according to claim 1, wherein the flexible sheet is on an exterior of the basket assembly.

13. A medical device according to claim 1, wherein the elongated member extends substantially to the handle.

14. A medical device according to claim 1, wherein the elongated member is coupled to the handle by another elongated member that extends substantially to the handle.

15. A medical device according to claim 1, wherein the flexible sheet comprises a laser resistant material.

16. A medical device, comprising:
a handle;
an elongated member having a proximal end and a distal end, the proximal end of the elongated member being coupled to the handle; and
a basket assembly having a proximal end and a distal end, the proximal end of the basket assembly being attached to the distal end of the elongated member, the basket assembly comprising a group of at least three supporting members and a flexible sheet attached to at least some of the supporting members in the group, the flexible sheet substantially covering the basket assembly except for a single side-facing opening when the basket assembly is in an expanded state, the side-facing opening extending at least partially between the proximal end of the basket assembly and the distal end of the basket assembly in the expanded state, the side-facing opening being substantially closed when the basket assembly is in a collapsed state; wherein said basket assembly is substantially free of elongated support members extending laterally across the gaps wherein a pair of supporting members defining the side-facing opening have lengths shorter than at least one other supporting member in the group and wherein distal ends of the pair of supporting members defining the side-facing opening are directly attached to one another at a point offset from an axis extending distally from the distal end of the elongated member.

17. A medical device according to claim 16, wherein the flexible sheet comprises a laser resistant material.

18. A medical device according to claim 17, wherein the elongated member includes a lumen to permit a laser lithotripsy device to be inserted into the basket assembly via the distal end of the elongated member.

* * * * *